United States Patent [19]
Webster et al.

[11] 4,208,353

[45] Jun. 17, 1980

[54] PRODUCTION OF FORMALDEHYDE

[75] Inventors: Dennis E. Webster; Ian M. Rouse, both of Royston, England

[73] Assignee: Johnson, Matthey & Co., Limited, London, England

[21] Appl. No.: 895,812

[22] Filed: Apr. 12, 1978

[30] Foreign Application Priority Data

Apr. 15, 1977 [GB] United Kingdom ............... 15761/77

[51] Int. Cl.² .............................................. C07C 45/16
[52] U.S. Cl. .................................. 568/472; 252/461; 252/459; 568/473; 568/474
[58] Field of Search ................... 260/603 C, 606, 602; 252/459, 461, 463, 465, 446, 47 L

[56] References Cited

U.S. PATENT DOCUMENTS

| | | | |
|---|---|---|---|
| 2,307,934 | 1/1943 | Coder et al. | 260/602 |
| 3,174,911 | 3/1965 | Webb et al. | 260/603 C |
| 3,965,195 | 6/1976 | Buschmann et al. | 260/603 C |

*Primary Examiner*—Werren B. Lone
*Attorney, Agent, or Firm*—Cushman, Darby & Cushman

[57] ABSTRACT

This invention relates to the production of formaldehyde and to catalysts therefor.

In particular the inventor relates to a process for the production of formaldehyde from methanol including the passage, at an elevated temperature, of a gas stream containing methanol and oxygen through a catalyst, the catalyst comprising a monolithic support provided with channels for passage therethrough of the gas stream and with the channel wall surfaces coated or impregnated with one or more elements selected from the group consisting of copper, silver, gold and iron.

5 Claims, No Drawings

PRODUCTION OF FORMALDEHYDE

This invention relates to the production of formaldehyde and to catalysts which may be used therefore.

It is known that formaldehyde may be manufactured by a combined oxidation and dehydrogenation using an air or oxygen plus methanol feedstock:

| CH₃OH | HCHO + H₂ |
|---|---|
| H₂ + ½O₂ | H₂O |

The catalyst most frequently used is pure silver in crystalline, i.e. granular, form in a catalyst bed.

According to the present invention a process for the production of formaldehyde from methanol includes the passage, at an elevated temperature, of a gas stream containing methanol and oxygen through a catalyst, comprising a monolithic support provided with channels for passage therethrough of the gas stream and with the channel wall surfaces coated or impregnated with one or more elements selected from the group copper, silver, gold and iron.

Preferably the elements copper, silver, gold and iron are in metallic form but they may be in chemically combined form. Alternatively the iron may be present in combined form as iron molybdate.

The invention also includes a catalyst comprising a monolithic support provided with channels for passage therethrough of reactants and with the channel wall surface coated or impregnated with one or more of elements selected from the group copper, silver, gold and iron.

By "elevated temperature" we mean a temperature such that when the gas stream is in contact with the catalyst a significant proportion of the methanol is converted to formaldehyde by the oxidative dehydrogenation reaction referred to above. The temperature is preferably within the range 500° C. –700° C.

The gas stream is preferably at a pressure within the range 0.5 to 2.0 atmospheres and has a space velocity through the catalyst within the range 5000 to 100000 hr.$^{-1}$. The gas stream passing through the catalyst normally also contains steam and recycled methanol.

The monolithic support may be either metallic or ceramic. Ceramic supports are preferably of the "honeycomb" type having a regular array of gas flow channels. Suitable materials which may be used to constitute the ceramic support are zircon-mullite, mullite, alpha alumina, sillimonite, magnesium silicates, kaolin clays, zircon, petalite, spodumene, cordierite and most aluminosilicates.

Proprietary products suitable for the monolithic support are described in U.S. Pat. No. 3,397,154 (Talsma), U.S. Pat. No. 3,498,927 (Stiles) and British Patent No. 882,484 (Corning). Examples are "Torvex" (Registered Trade Mark) which in one convenient form is a mullite honeycomb having eight corrugations per inch and an alumina washcoat; "Thermacomb" (Registered Trade Mark), a cordeirite honeycomb supplied by the Minnesota Mining and Manufacturing Corporation and M20 a cordierite honeycomb supplied by Corning Glass.

Preferably the ceramic honeycomb structure has deposited thereon a first coating of a refractory metal oxide which is then further impregnated or coated with one or more of the catalytic metals specified above. Suitable refractory metal oxides comprising the said first coating are one or more of the oxides of B, Al, Si, Be, Mg, Ca, Sr, Ba, Sc, Y, Ti, Zr, Hf, Th, the lanthanides and the actinides. Preferred refractory metal oxide layers comprise members of the gamma or activated alumina family. This can be prepared, for example, by precipitating a hydrous alumina gel and, thereafter, drying and calcining to expel hydrated water and provide active gamma alumina. We prefer to use British Aluminium Co. FRF 80 alumina tri-hydrate and convert it to activated alumina by drying and firing as described above.

A metallic monolith support is preferred to a ceramic support. As supports, metallic monoliths give a lower pressure drop and possess 1½–3 times the surface to volume ratio obtained with a ceramic honeycomb substrate. The normal ceramic substrate surface area is 600 –700 sq. ft. per cubic foot of substrate. Examples are proprietary products M20 (Corning) which has a surface area of 576 sq. ft/ft³ and Grace 400 cell which is 760 sq. ft/ft³. This is the highest obtained so far and should be compared with 1100 sq. ft/ft³ for 0.003" thick metal and 2000 sq. ft/ft³ for 0.002" thick metal sheet.

We prefer to use foil of thickness between 0.0015 and 0.0045 inch and more preferably of thickness 0.002 inch corrugated and assembled to form a structure having approximately 400 cells per square inch when considered in cross-section. A preferred range of cell sizes is 200 –800 cells per square inch. Suitable surface to volume ratios are 1200 sq. ft. per cubic foot with 400 cells per square inch and 2000 sq. ft. per cubic foot with 800 cells per square inch.

In one embodiment of the invention the catalytic metals Cu, Au, Ag and Fe as defined herein may be fabricated in the form of metallic foil monolith direct. For example a Cu-Ag foil monolith can be used. Other metals which may be used for fabrication of the monolith support are those capable of withstanding high temperature and rigorous oxidising conditions. Examples of such base metal alloys are nickel and chromium alloys having an aggregate Ni + Cr content greater than 20% by weight and alloys of iron including at least one of the elements chromium (3–40 wt %), aluminium (1–10 wt %), cobalt (trace —5 wt %), nickel (trace —72 weight %) and carbon (trace —0.5 weight %). Quantities of trace elements which may usefully be present in such alloys to improve strength and oxidation - and heat-resistance are:

|    | %    | W/W  |
|----|------|------|
| Si | 0.2  | 0.9  |
| Mn | 0.2  | 0.7  |
| Zr | 0.01 | 0.20 |
| Cu | 0.01 | 0.15 |
| Nb | 0.01 | 0.3  |
| Ta | 0.8  | 1.2  |
| Ti | 0.8  | 1.2  |
| Co | 0.01 | 1.0  |
| Ca | 0.01 | 0.5  |
| C  | 0.01 | 0.1  |

One range of heat resistant alloys which may comprise the extended metal substrate are preferably those alloys having a minimum nickel plus chromium content of 20% by weight. Typical alloys which therefore may be used for the extended metal substrate are high nickel and chromium stainless steels and proprietary products such as "INCONEL" (Registered Trade Mark) 600 and "INCONEL" 601.

Other examples of base metal alloys capable of withstanding the rigorous conditions required are the iron-aluminium-chromium alloys which also contain yttrium. These contain 0.5-12 wt % Al, 0.1-3.0 wt % Y, 0-20 wt % Cr and balance Fe. These are described in U.S. Pat. No. 3,298,926. Another range of Fe-Cu-Al-Y-alloys contain 0.5-4 wt % Al, 0.5-3.0 wt % Y, 20.0-95.0 wt % Cr and balance Fe. These are described in U.S. Pat. No. 3,027,252.

An example of a metallic substrate made in accordance with this invention comprises a roll of corrugated sheet of a heat resistant alloy, or of the catalytic metal, interleaved with a non-corrugated sheet of such an alloy or metal. Alternatively two corrugated sheets may be used with the corrugations in each sheet parallel with each other or at an angle to each other. Other ways of producing channels in the substrate include crimping, folding, indenting and perforating one or both of the sheets. The surface area of substrates made in thin metals by these techniques is normally much greater than that obtained with ceramic honeycombs or with particulare catalyst supports of the same overall volume. A coiled substrate may then be provided with a firmly adherent oxide coating which is porous and absorbent and has a high surface area and which acts as the carrier for the second catalytically active layer containing one or more of the catalytic metals as herein defined.

We prefer to provide the metallic substrate with a first firmly adherent oxide layer in an essentially two stage process. In a first stage the metallic substrate is oxidised to provide a thin first oxide layer which acts as a key. A preferred method is to carry out thermal oxidation by maintaining the formed metallic substrate at from 1000-1200° C. in air or moist cracked ammonia vapour for 1 hour. The higher temperature is required with very oxidation resistant alloys such as the Kanthal range and the moist hydrogen atmosphere is preferred with alloys having a high Ni content.

In a second stage the adherent oxygen containing or oxide film may be produced by any one of several known methods including chemical techniques. The film must be of sufficient thickness to provide adequate absorbtive capacity for retaining the catalytically active alloy comprising one or more of the platinum group metals. The film is preferably from 0.0004 to 0.001 inch thick.

Where aluminium is present in the alloy forming the extended metal substrate the first stage oxide film may be produced by treating the aluminium containing surface with a solution of an alkaline carbonate usually a sodium carbonate chromate solution. The film may be produced by the anodic oxidation of the metal surface whereby the metal is made the anode in an electrolytic solution. In anodising aluminium containing surfaces, a 15% sulphuric acid solution is commonly employed as the electrolyte but other acid electrolytes such as chromic acid, oxalic acid, phosphoric acid and sometimes boric acid may be used. The oxide film to which this invention relates is deliberately positioned and does not include the relatively thin natural oxide films which sometimes occur on metal surfaces which have been exposed to the atmosphere.

One method of forming a first stage alumina layer on these alloys which do not contain sufficient aluminium to form their own alumina layer upon oxidation is the use of Calorising (Registered Trade Mark). This involves the vapour deposition of an aluminium coating followed by anodising or heating in an oxygen-containing gas. Alternative coatings such as chromate, phosphate, silica or silicate or zirconia may all be deposited by known methods.

There are many different techniques for the preparation of the second stage high surface area catalytically active refractory metal oxide wash coat containing one or more of the refractory metal oxides which confer beneficial properties as regard ageing and inertness to deposited catalytic metals at high temperature under oxidising and reducing conditions. Some of these are described below:

A preferred adherent oxide coating deposited upon the extended metal subsrate is alumina.

One method for the deposition of hydrous alumina is proposed in U.S. Pat. No. 12,406,420. Any convenient aluminium compound such as alkali metal aluminates and aluminium salts may be used as the starting material. Either acidic or basic precipitants are used, depending upon the character of the starting material. Suitable acidic precipitants are ammonium chloride, ammonium sulphate, ammonium nitrate, hydrochloric acid, nitric acid, etc. Suitable basic precipitants are ammonium hydroxide, sodium hydroxide, hexa-methylene, tetramine, etc.

Another method is to precipitate the hydrous alumina from an alkali metal hydroxide directly on to the extended metal substrates forming part of the present invention. If the aluminate solution is maintained at a temperature of 60°-85° C. a film or coating of alpha alumina trihydrate (Gibbsite) is deposited. Subsequent heating at from 25°-180° C. converts the monohydrate to gamma alumina without loss of the very high surface area coating which is produced by this method. The high surface area results from the formation of hexagonal crystal aggregates of approximate size $8 \times 8 \times 20$ microns. Micropores of size 40 Å diameter are present in the hexagonal crystal aggregates but appear to play no part in the catalytic activity of the structure.

We prefer a washcoat loading which is within the range of 5-30% by weight of the metallic monolith substrate. A suitable loading of $Al_2O_3$ on Kanthal D having 400 cells per square inch is 10% by weight. The surface area of the alumina is 50-500 square metres per gram of alumina. The aluminate method of deposition of alumina, described above, gives a surface area of from 120-160 square metres per gram of alumina.

An alternative preferred method for the deposition of an adherent alumina washcoat on the metallic substrate is to prepare a slurry of a pre-activated Gibbsite (alumina trihydrate) and an alumina monohydrate having a solid liquid ratio of between 25 and 25% and a pH less than 7 and using this to impregnate the shaped substrate by complete immersion. The exact strength of the slurry used (which may be determined by trial and error) should be sufficient to produce an alumina washcoat of the required thickness. The substrate is then allowed to dry in warm air and finally fired for 2 hours at 450° C. to form chi and gamma alumina in adherent coating up to 0.002 in. thick on themetallic substrate. Crystal aggregates of diameter 3-7 microns are produced having micropores of approximately the same size, i.e. 40Å in diameter.

A further alternative method of deposition of an adherent alumina washcoat on the metallic substrate is to use a slurry of alpha alumina monohydrate. After firing at 450° C. gamma alumina is formed having a surface area generally between 180 and 300 square metresper gam. Gamma alumina is added to alphga alumina monohydrate at the slurring stage before firing in order to form a thixotropic mixture. Cry-stallite or crystal aggregates of 20-100Å diameter are formed. Micropore diameters remain the same at 40Å.

Suitable proprietary alumina trihydrates (Gibbsite) are "FRF 80" supplied by British Aluminium Chemicals Ltd. and "C 333" supplied by Reynolds. Suitable alumina monohydrates (Boehmite) are "Sol-Gel Alumina" supplied by the United Kingdom Atomic Energy Authority. "Dispal M" supplied by Conoco and "Condea F" also supplied by the Conoco Group. Gibbsite is added to "Sol-Gel Alumina" (which is microcrystalline Boehmite) at the slurring stage in order to form a thixotropic mixture.

Optionally one or more of the oxides titania, zirconia, hafnia, and thoria may be present in the alumina for the purpose of providing additional stabilisation of the intermediate oxide (washcoat) layer. Other rare earth oxides, alkaline earth oxides and alkali metal oxides may also be used.

Many of the aluminium-containing metallic substrates according to the present invention have the property of oxidising "inwards". That is to say we believe that a factor contributory to the success of the present invention is the fact that the extended metal substrate itself, which forms part of the catalytic structure of the present invention has a tendency to oxidise under very strongly oxidising conditions in such a way that the firstlayer of adherent oxide film does not tend to grow over or conver the outermost layer of the catalytic metal, iron, copper, silver or gold.

Impregantion or deposition of one or more of the catalytic metals, upon the first refractory metal oxide containing adherent layer may be accomplished by known methos of deposition of catalytically active metals on washcoats or other supports, e.g. if a high surface area refractory metal oxide is the adherent oxygen containing film, the support may be immersed in a solution of water soluble inorganic salt or salts of the metal. In the case of silver a suitable method used would be immerse the oxide coated substrate in a bath containing hot ammoniacal sivler nitrate. On removing the unit from the bath the excess solution is drained before allowing the monolith to dry. The impregnated silver species may then be reduced to metallic silver by immersing in a bath of boiling water containing approximately 10 grams/liter dextrose. The bath is maintained at approximately pH8 by the addition of sodium bicarbonate. The catalyst thus obtained is again drained and dried.

If the catalytic metal is iron, present as iron molybdate, this may be present in one of the forms $FeMoO_4$, $Fe_2(MoO_4)_3$, $Fe_2(MoO_4)_3 MoO_3$. Iron (as one of the forms of iron molydate) and silver are the preferred catalytic metals for deposition on the monolith.

The product gases pass through a water cooled condenser where a proportion of the formaldehyde, unreacted methanol and steam are condensed.

A subsequent absorber scrubs the remaining gases in a circulating formaldehyde (Formalin) solution. Formic acid produced may be removed by an ion exchange resin.

The invention includes formaldehyde and formalin when made by a process according to the present invention.

What we claim is:

1. A process for the production of formaldehyde from methanol by oxidative dehydrogenation which comprises passing gaseous methanol and oxygen at an elevated temperature in the range of 500° C.–700° C., a pressure of 0.5 to 2.0 atmospheres and a space velocity in the range of 5000 to 100,000 $hr^{-1}$ through a catalyst comprising a monolithic metal or ceramic support provided with channels for passage therethrough of the gas stream, the channel wall surfaces being coated or impregnated with one or more elements selected from the group consisting of copper, silver, gold and iron.

2. A process according to claim 1 wherein the elements copper, silver, gold and iron are in metallic form.

3. A preocess according to claim 1 wherein, the elements copper, silver, gold and iron are in chemically combined form.

4. A process according to claim 1, in which iron is present as iron molybdate.

5. A process according to claim 1 wherein the gas stream contains steam and recycled methanol.

* * * * *